(12) United States Patent
Hsu

(10) Patent No.: US 6,796,961 B1
(45) Date of Patent: Sep. 28, 2004

(54) SAFETY HYPODERMIC SYRINGE

(76) Inventor: Fu-Yu Hsu, No.407, Kuo Chi Road, Sec.2, Tayuan Hsiang, TaoYuan Hsien (TW)

( * ) Notice: Subject to any disclaimer, the term of this patent is extended or adjusted under 35 U.S.C. 154(b) by 0 days.

(21) Appl. No.: 10/384,611

(22) Filed: Mar. 11, 2003

(51) Int. Cl.⁷ .................................................. A61M 5/00
(52) U.S. Cl. ...................................... 604/110; 604/192
(58) Field of Search .................................. 604/192, 198, 604/187, 263, 110, 195, 131, 132, 193, 194, 196, 197

(56) References Cited

U.S. PATENT DOCUMENTS 4,986,813 A  *  1/1991  Blake et al. ................. 604/110
5,393,301 A  *  2/1995  Goldberg ..................... 604/110

* cited by examiner

*Primary Examiner*—Manuel Mendez
(74) *Attorney, Agent, or Firm*—Rosenberg, Klein & Lee

(57) ABSTRACT

A safety hypodermic syringe in which the needle hub of the needle assembly has two sliding grooves respectively coupled to respective small stub rods in the socket at the front side of the barrel so that the needle assembly is moved backwards and received inside the barrel upon a return stroke of the plunger after the service of the safety hypodermic syringe and after a rotation of the plunger through an angle relative to the barrel.

7 Claims, 12 Drawing Sheets

SAFETY HYPODERMIC SYRINGE

BACKGROUND OF THE INVENTION

1. Field of the Invention

The present invention relates generally to a hypodermic syringe and, more particularly, to a safety hypodermic syringe, which enables the needle assembly to be automatically received inside the barrel upon a return stroke of the plunger after a rotary motion of the plunger.

2. Description of the Related Art

When disposing of a disposable hypodermic syringe after its service, the person handling the disposable hypodermic syringe may be injured by the protruding needle cannula accidentally. In order to eliminate this problem, safety hypodermic syringes are developed. These safety hypodermic syringes enable the needle assembly to be pulled backwards with the plunger and received inside the barrel after the service. Exemplars of these safety hypodermic syringes are seen in Taiwan Patent Publication Nos. 189436; 356013; 463639; 414085; 384709; 359621; 492328; 467752; 475449; 480185; 497976; 430565; 471322; 332433; 394027; and 447310, and U.S. Pat. Nos. 5,385,557; 4,747,830; 4,677,980; 5,242,400; 4,986,813; 4,947,863; 5,533,975; 5,171,300; 4,944,723; . . . etc.

FIG. 1 shows a safety hypodermic syringe according to the prior art. According to this design, the safety hypodermic syringe comprises a barrel 11, the barrel 11 having a front socket 12 and two raised portions 121 protruding from the inside wall of the front socket 12, a needle hub 13 mounted in the front socket 12, the needle hub 13 having two angled crevices 131 extended to the front side and respectively coupled to the raised portions 121 of the front socket 12, and a bottom retaining hole 132, and a plunger and stopper assembly 14 inserted into the barrel 11 from the rear side, the stopper assembly 14 having a front engagement tip 141 adapted to engage the bottom retaining hole 132 of the needle hub 13. FIG. 2A shows the safety hypodermic syringe assembled. This design of safety hypodermic syringe is seen in U.S. Pat. No. 5,273,543. It has drawbacks as outlined hereinafter.

1. The raised portions 121 of the front socket 12 are respectively stopped at the end of the rear horizontal section of the angled crevices 131 when the safety hypodermic syringe assembled. When removing the needle hub 13 from the front socket 12 after the service of the hypodermic syringe, the user must rotate the needle hub 13 with the plunger 14 in the assigned direction. When rotating the plunger 14 in the wrong direction, the connection between the needle hub 13 and the raised portions 121 of the front socket 12 is reinforced, unable to remove the needle hub 13 from the raised portions 121.

2. Because the contact 15 between the needle hub 13 and the front socket 12 is a planar contact, the outer diameter of the needle hub 13 must be made to be press-fitted into the inner diameter of the front socket 12 to prevent a leakage. Due to high friction resistance between the outside wall of the needle hub 13 and the inside wall of the front socket 12, the user must employ much effort to the plunger 14 to pull the needle hub 13 and the needle cannula 133 back to the inside of the barrel 11 after the service of the safety hypodermic syringe (see FIG. 2B).

There are known other designs of safety hypodermic syringes that use a screw joint to secure the neck hub in position. These designs are seen in U.S. Pat. Nos. 4,944,723; 4,978,340; 5,171,300; 4,947,863; 4,986,813. Other needle hub positioning designs are seen in Taiwan Patent Publication Nos. 492328; 356013; 359621; 463639, etc., and U.S. Pat. Nos. 5,242,400; 4,747,830; 5,098,390; 5,370,619; 4,911,693, etc. These prior art designs still cannot eliminate the aforesaid drawbacks.

Therefore, it is desirable to provide a safety hypodermic syringe that eliminates the aforesaid drawbacks.

SUMMARY OF THE INVENTION

The present invention has been accomplished under the circumstances in view. It is the main object of the present invention to provide a safety hypodermic syringe, which enables the needle assembly to be conveniently received inside the barrel after the service of the safety hypodermic syringe. It is another object of the present invention to provide a safety hypodermic syringe, which enables the needle assembly to be automatically received inside the barrel upon a return stroke of the plunger after a rotary motion of the plunger.

To achieve these and other object of the present invention, the safety hypodermic syringe comprises a barrel, the barrel comprising a body and a socket at a front side of the body; a needle assembly, the needle assembly comprising a needle hub mounted in the front socket of the barrel, the needle hub having a bottom coupling hole, and a needle cannula forwardly extended from the needle hub outside the barrel; and a plunger and stopper unit, the plunger and stopper unit comprising a stopper fitted into the body of the barrel, and an elongated plunger backwardly extended from the stopper to the outside of the barrel and adapted to reciprocate the stopper in the body of the barrel, the stopper having a front engagement tip adapted to engage the bottom coupling hole of the needle hub for enabling the needle assembly to be pulled backwards with the plunger and stopper unit and received inside the body of the barrel. The socket of the barrel has at least one small stub rod protruding from the inside wall. The needle hub of the needle assembly comprises at least one sliding groove formed in the periphery and respectively coupled to the at least one small stub rod of the socket, for enabling the needle assembly to be pulled backwards with the plunger and stopper unit and received inside the body of the barrel after a rotary motion of the plunger relative to the barrel. The at least one sliding groove each has two distal open ends through which the at least one small stub rod of the socket is moved in and out of the at least one sliding groove when the plunger and stopper unit and the barrel are rotated relative to each other, and a positioning portion on the middle between the two distal open ends for engagement with the at least one small stub rod of the socket. Further, the sliding grooves of the needle hub can be made having a substantially U-shaped profile, or a V-shaped profile.

DETAILED DESCRIPTION OF THE INVENTION

Figure 1:
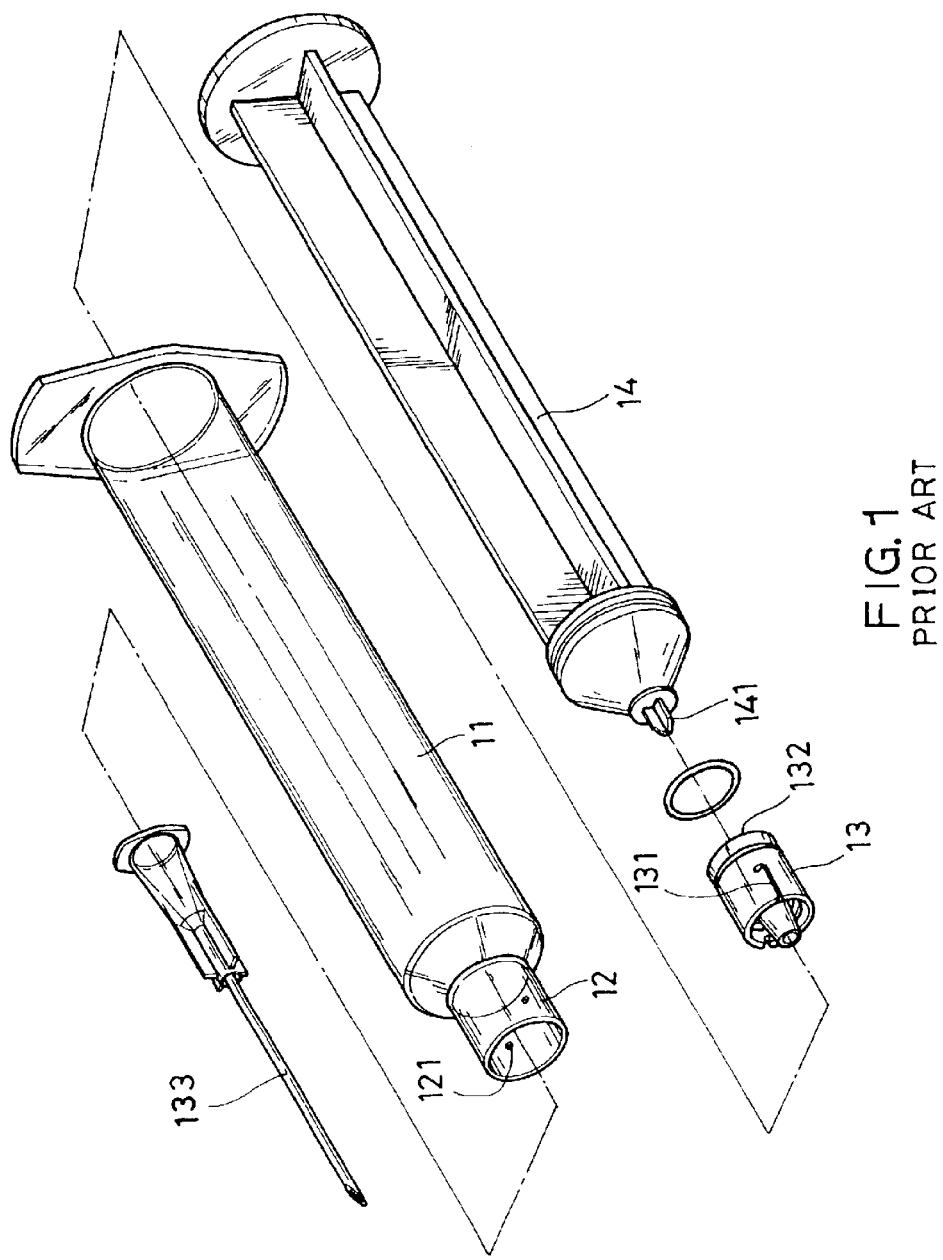
FIG. 1 is an exploded view of a safety hypodermic syringe according to the prior art.
Figures 2A, 2B:
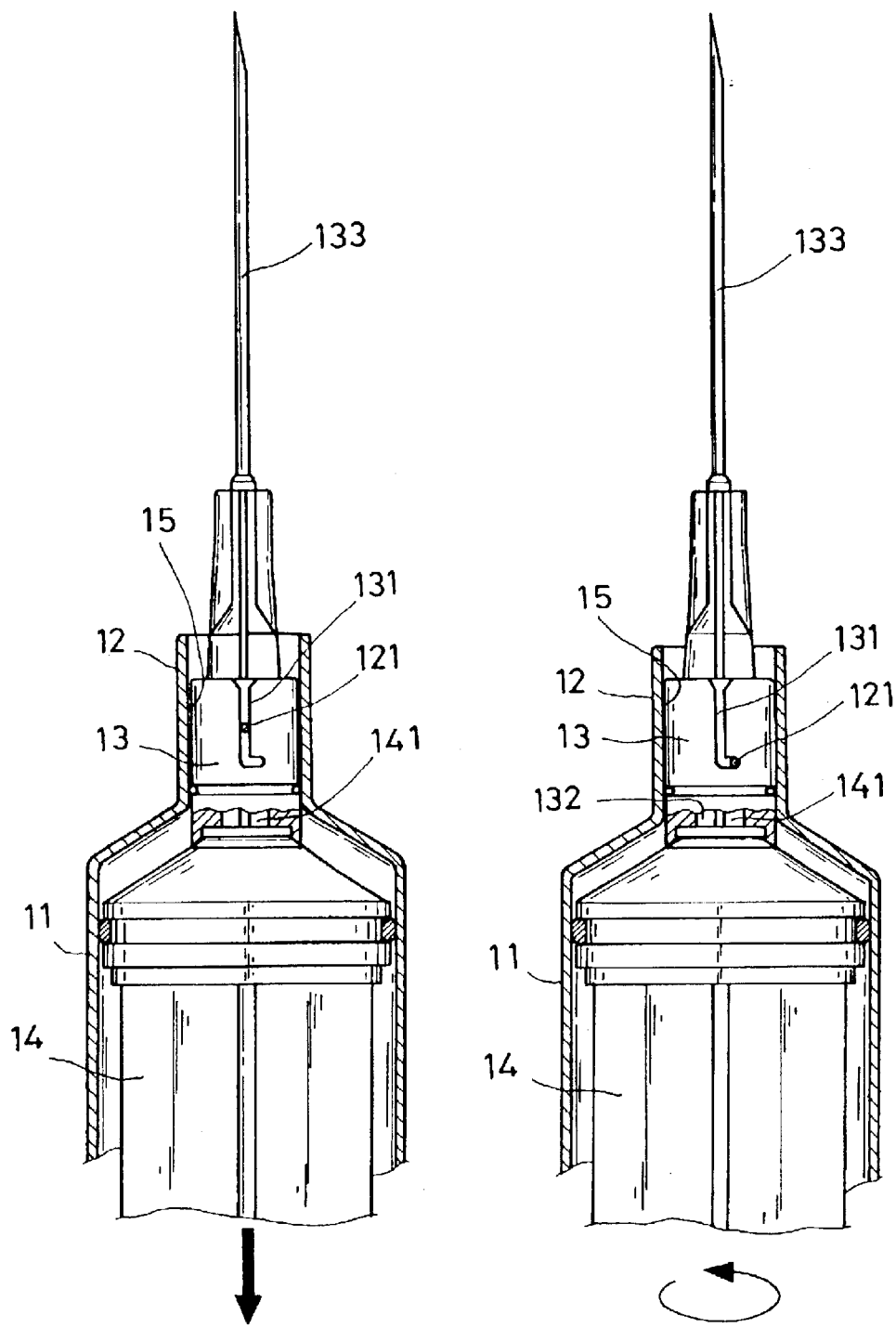
FIG. 2A is a sectional side assembly view in an enlarged scale of the prior art safety hypodermic syringe shown in FIG. 1.
FIG. 2B is similar to FIG. 2A but showing the plunger moved backwards.
Figure 3:
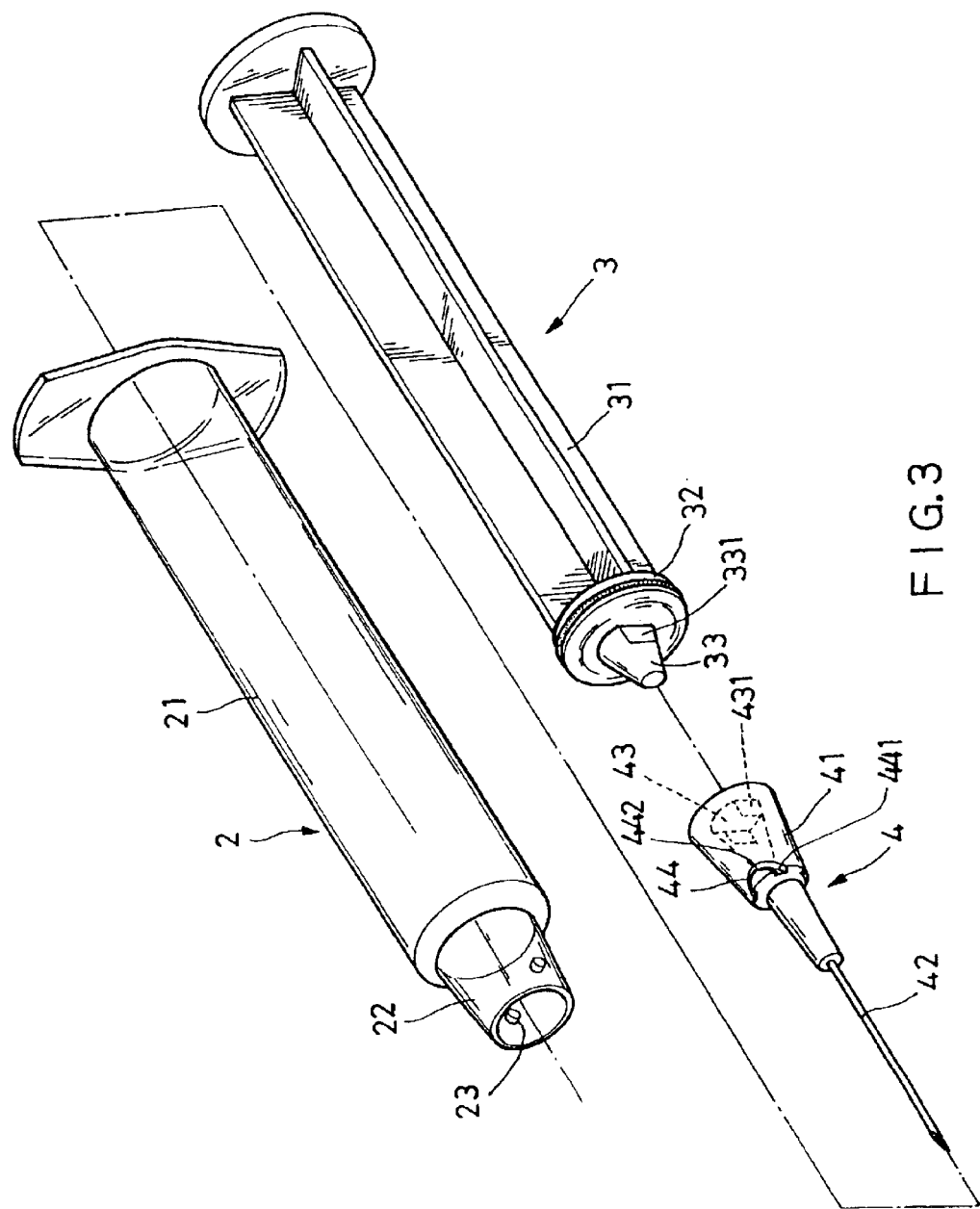
FIG. 3 is a perspective exploded view of a safety hypodermic syringe according to the present invention.
Figure 4:
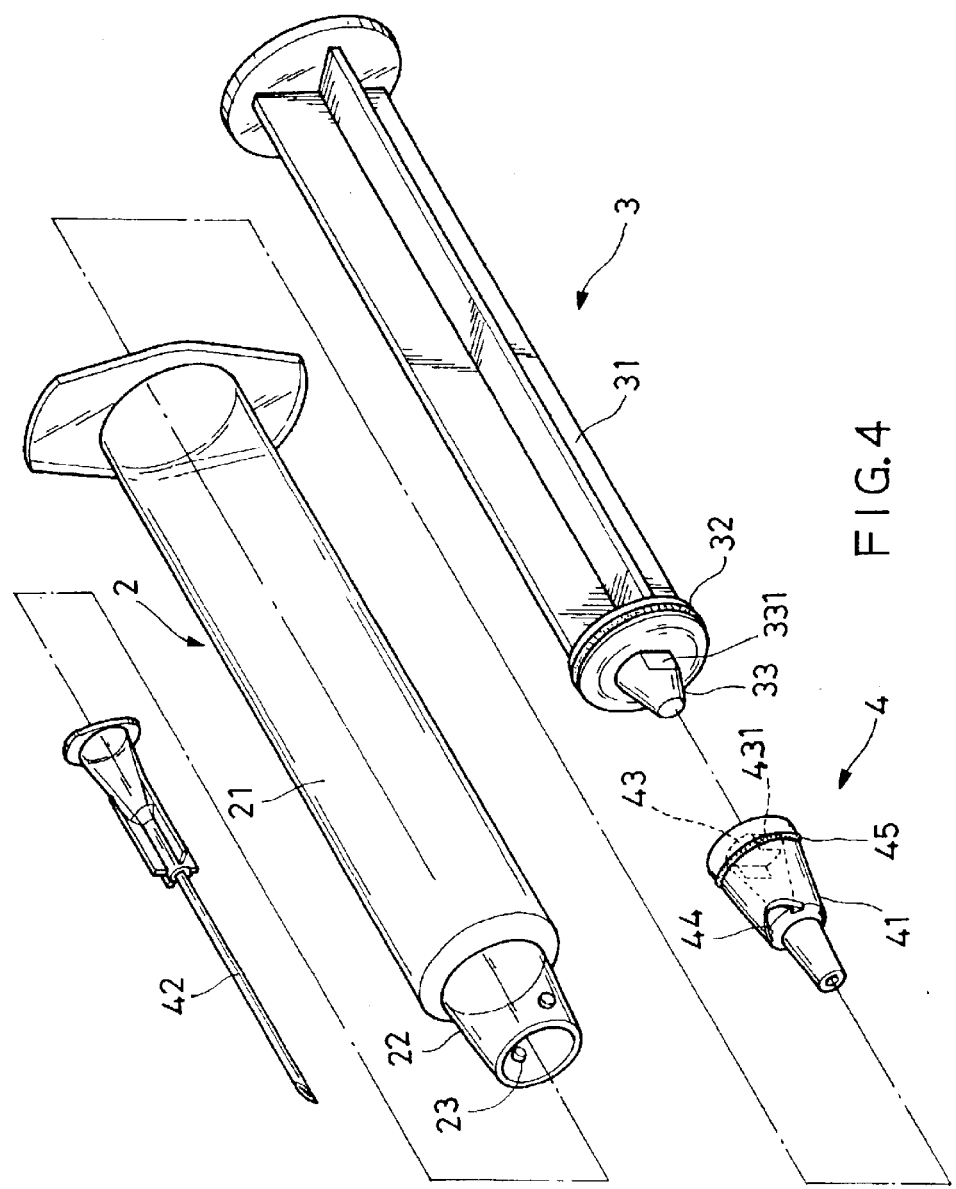
FIG. 4 is a perspective exploded view of an alternate form of the safety hypodermic syringe according to the present invention.

Referring to FIG. 3, a safety hypodermic syringe in accordance with the present invention is shown comprised of a barrel 2, which comprises a body 21, a socket 22 at the front side of the body 21, and at least one, two example, two small stub rods 23 symmetrically protruded from the inside wall of the socket 22, a plunger and stopper unit 3, which comprises a stopper 32 fitted into the body 21 of the barrel 2 and an elongated plunger 31 axially extended from the rear side of the stopper 32 and adapted to reciprocate the stopper 22 in the body 21 of the barrel 2, and a front engagement tip 33 shaped like a truncated cone and forwardly protruded from the front side of the stopper 32 at the center and having at least one, for example, two planes 331 at two sides, and a needle assembly 4, which comprises a needle hub 41 mounted in the front socket 22 of the barrel 2 and a needle cannula 42 forwardly extended from the needle hub 41 outside the barrel 2. The needle cannula 42 may be formed integral with the front side of the needle hub 41. Alternatively, the needle hub 41 and the needle cannula 42 can be independent members fastened together (see FIG. 4). Further, a rubber ring 45 may be fastened to the periphery of the needle hub 41 as shown in FIG. 4. Further, the needle hub 41 has a bottom coupling hole 43 and two planes 431 symmetrically disposed in the bottom coupling hole 43 at two sides corresponding to the planes 331 of the front engagement tip 33.

Figure 5:
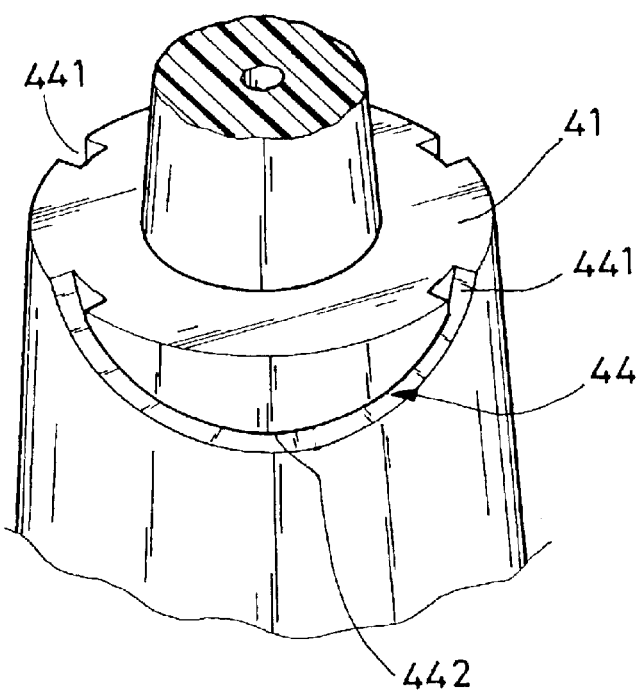
FIG. 5 is an enlarged view in an enlarged scale of a part of the needle hub according to the present invention.
Figure 6:
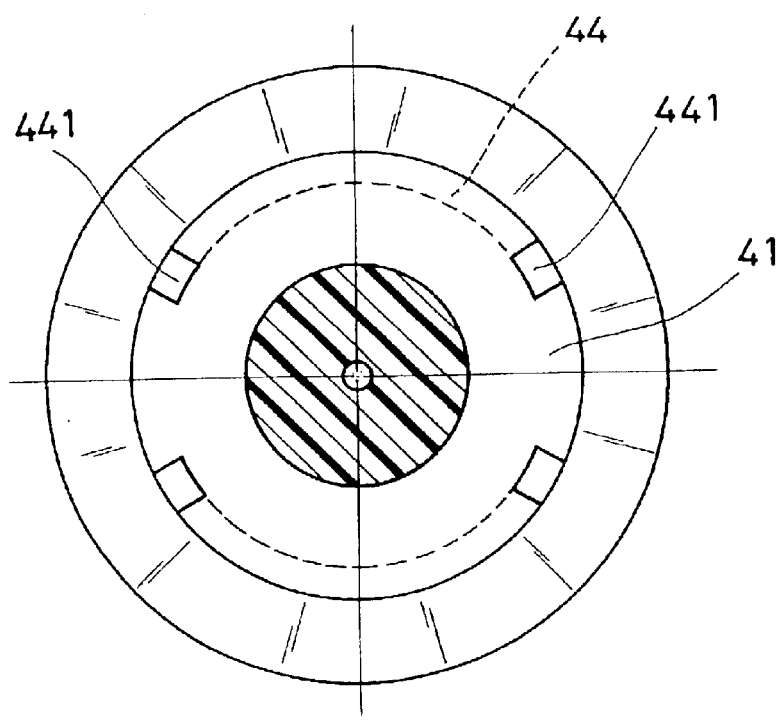
FIG. 6 is a bottom view of FIG. 5.
Figure 7A:
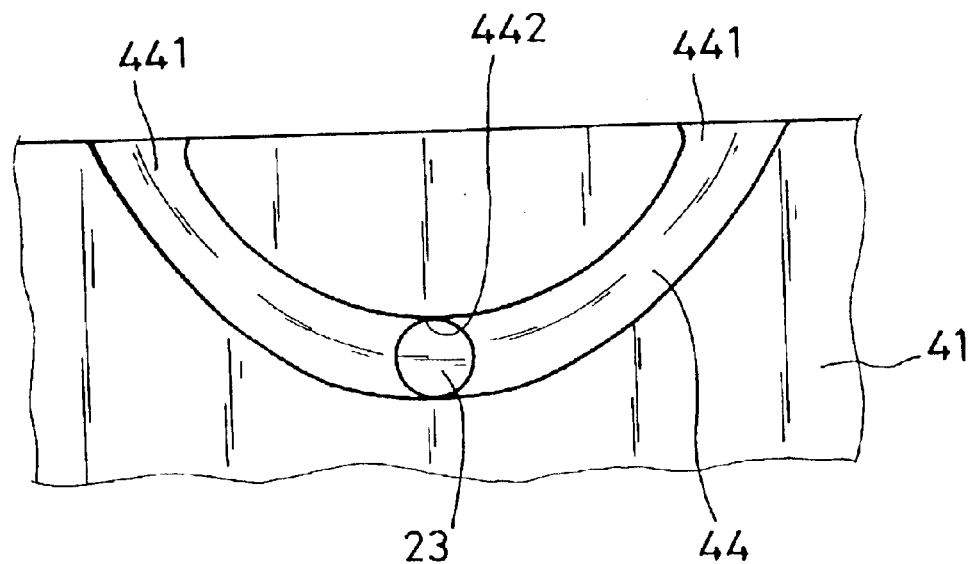
FIG. 7A is a schematic drawing showing one example of the sliding groove of the needle hub according to the present invention.
Figure 7B:
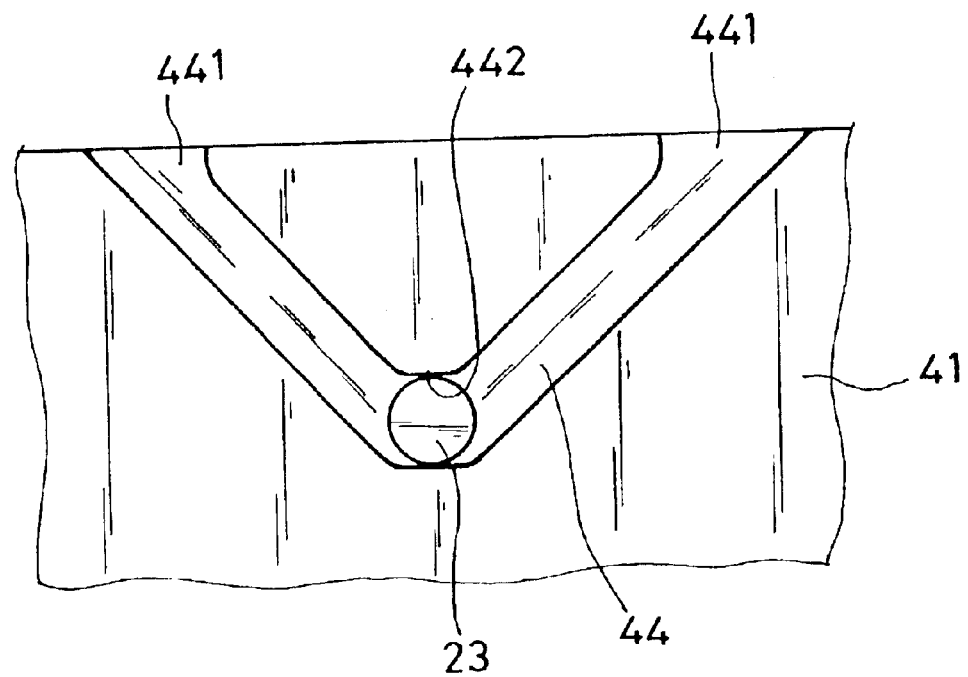
FIG. 7B is a schematic drawing showing another example of the sliding groove of the needle hub according to the present invention.

Referring to FIGS. 5 and 6 and FIG. 3 again, the needle hub 41 comprises two smoothly curved sliding grooves 44 symmetrically disposed at two sides and respectively coupled to the small stub rods 23 in the socket 22 of the barrel 2. Each sliding groove 44 has two distal open ends 441 and a positioning portion 442 disposed on the middle at the lowest point. The sliding grooves 44 may be made having a substantially U-shaped profile as shown in FIG. 7A, or a substantially V-shaped profile as shown in FIG. 7B. Each sliding groove 44 symmetrically downwardly curves from the respective two distal open ends 441 to the respective positioning portion 442.

Figure 8:
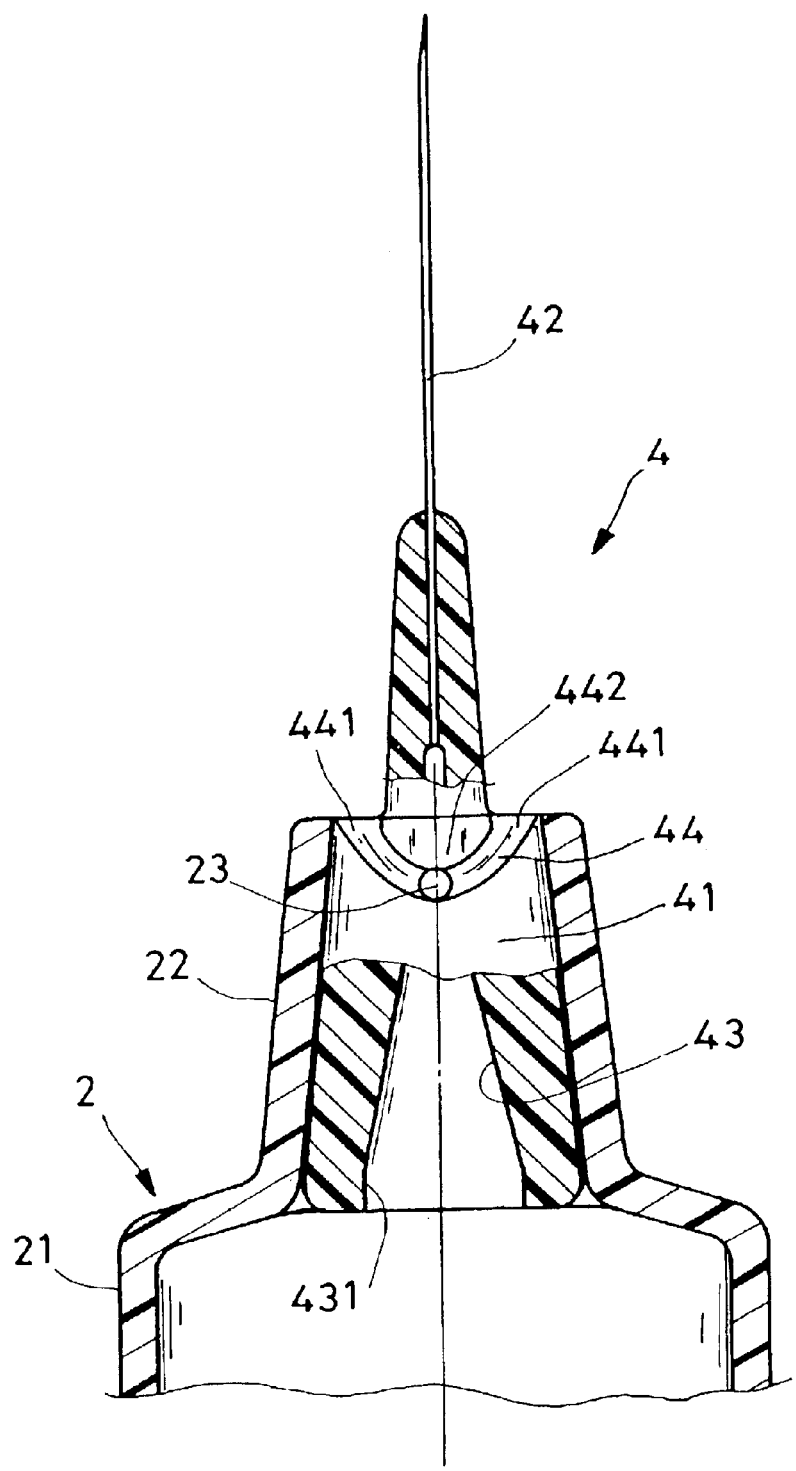
FIG. 8 is a sectional assembly view in an enlarged scale of a part of the safety hypodermic syringe according to the present invention, showing the needle hub positioned in the socket of the barrel.

Referring to FIG. 8, when fastening the needle hub 41 to the socket 22 of the barrel 2, one open end 441 of each sliding groove 44 is respectively attached to the small stub rods 23 inside the socket 22 of the barrel 2, and then the needle hub 41 is rotated in the socket 22 in one direction through an angle, enabling the small stub rods 23 to be respectively moved to the positioning portions 442 of the sliding grooves 44 and firmly secured thereto by means of friction resistance. Preferably, the socket 22 is a tapered socket having an inner diameter gradually reduced from the rear side (the side connected to the body 21 toward the front side (the side remote from the body 21), and the needle hub 41 is a stepped conical member having an outer diameter fitting the inner diameter of the socket 22. The connection between the socket 22 and the needle hub 41 becomes firmly when the needle hub 41 pulled forwards relative to the socket 22.

Figure 9:
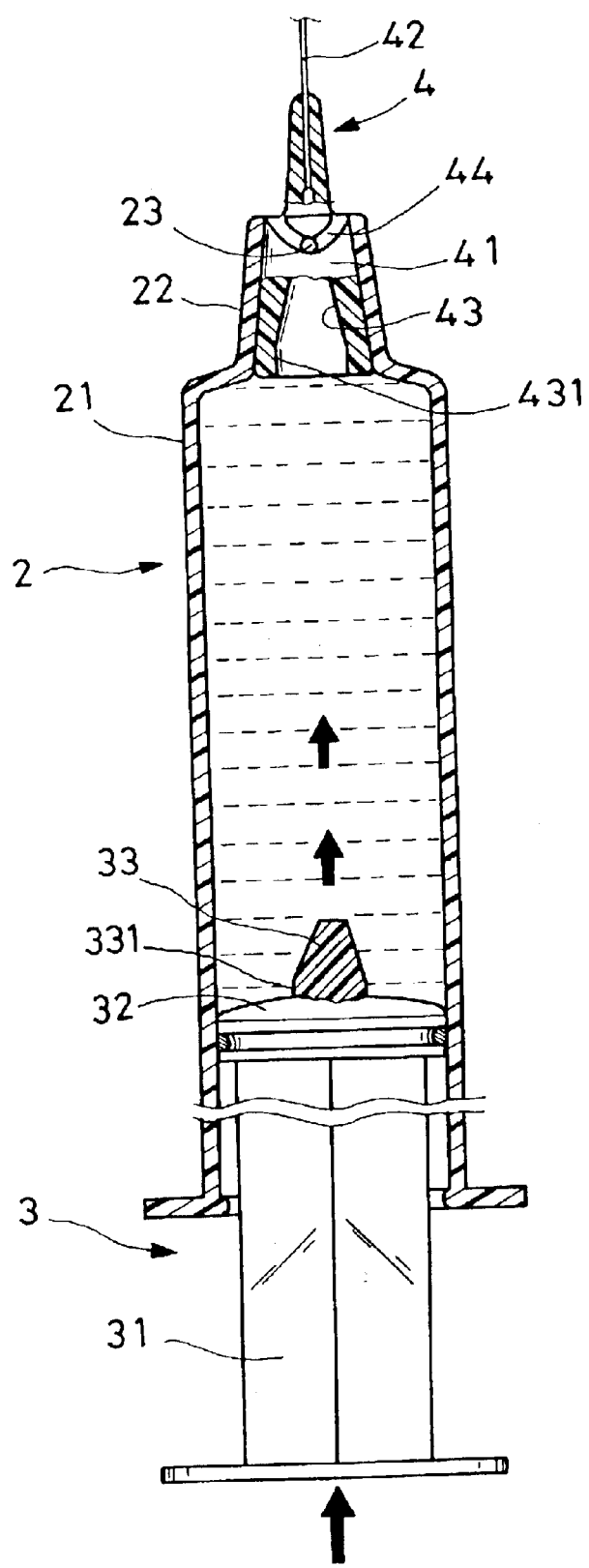
FIG. 9 is a schematic side view of the present invention, showing a status of the use of the safety hypodermic syringe.
Figures 10, 11:
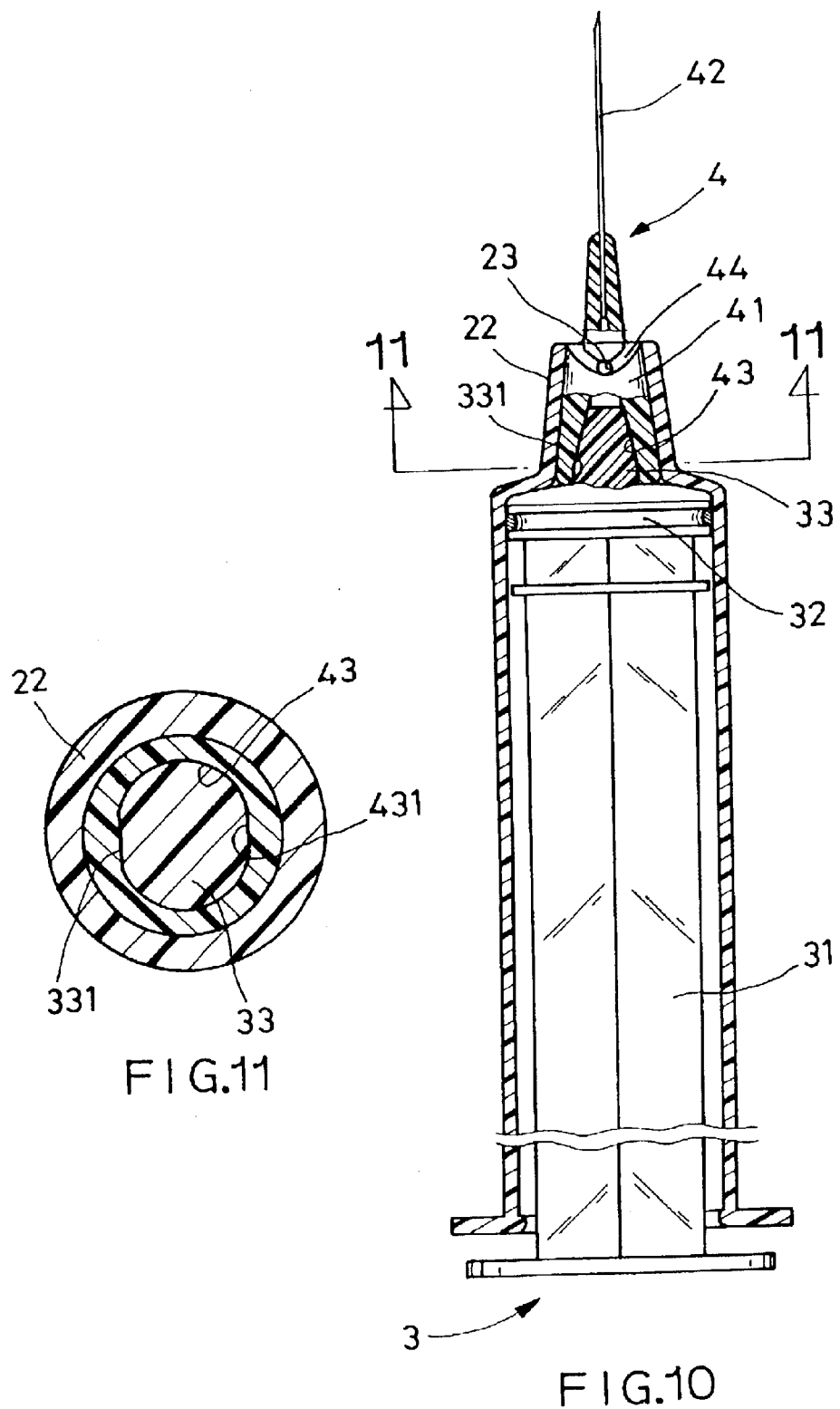
FIG. 10 is a sectional view in an enlarged scale of the safety hypodermic syringe according to the present invention, showing the status of the hypodermic syringe after injection.
FIG. 11 is a sectional view taken along line 11—11 of FIG. 10.
Figure 12A:
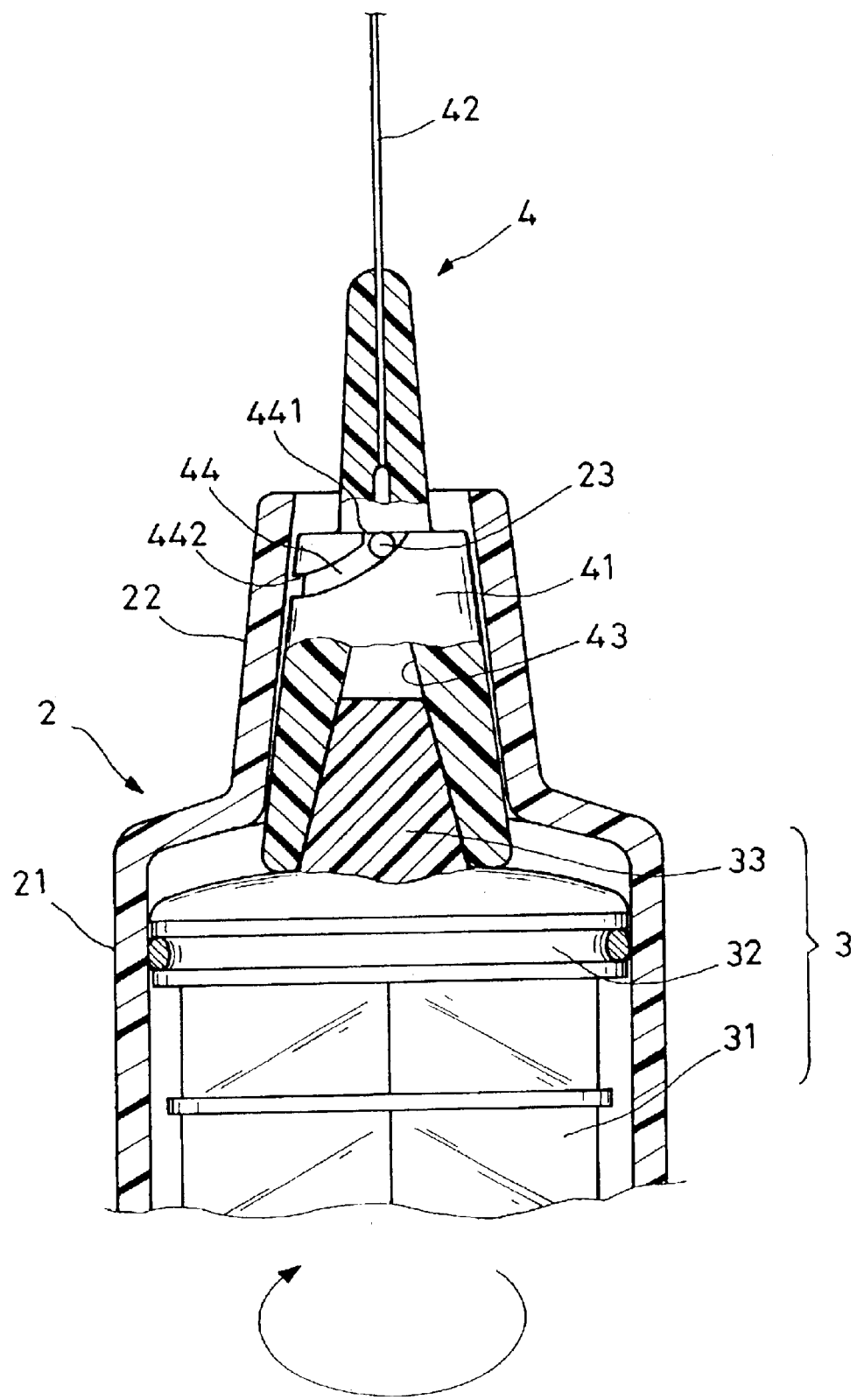
FIG. 12A is a schematic side view of the present invention, showing the plunger rotated clockwise relative to the barrel after injection.
Figure 12B:
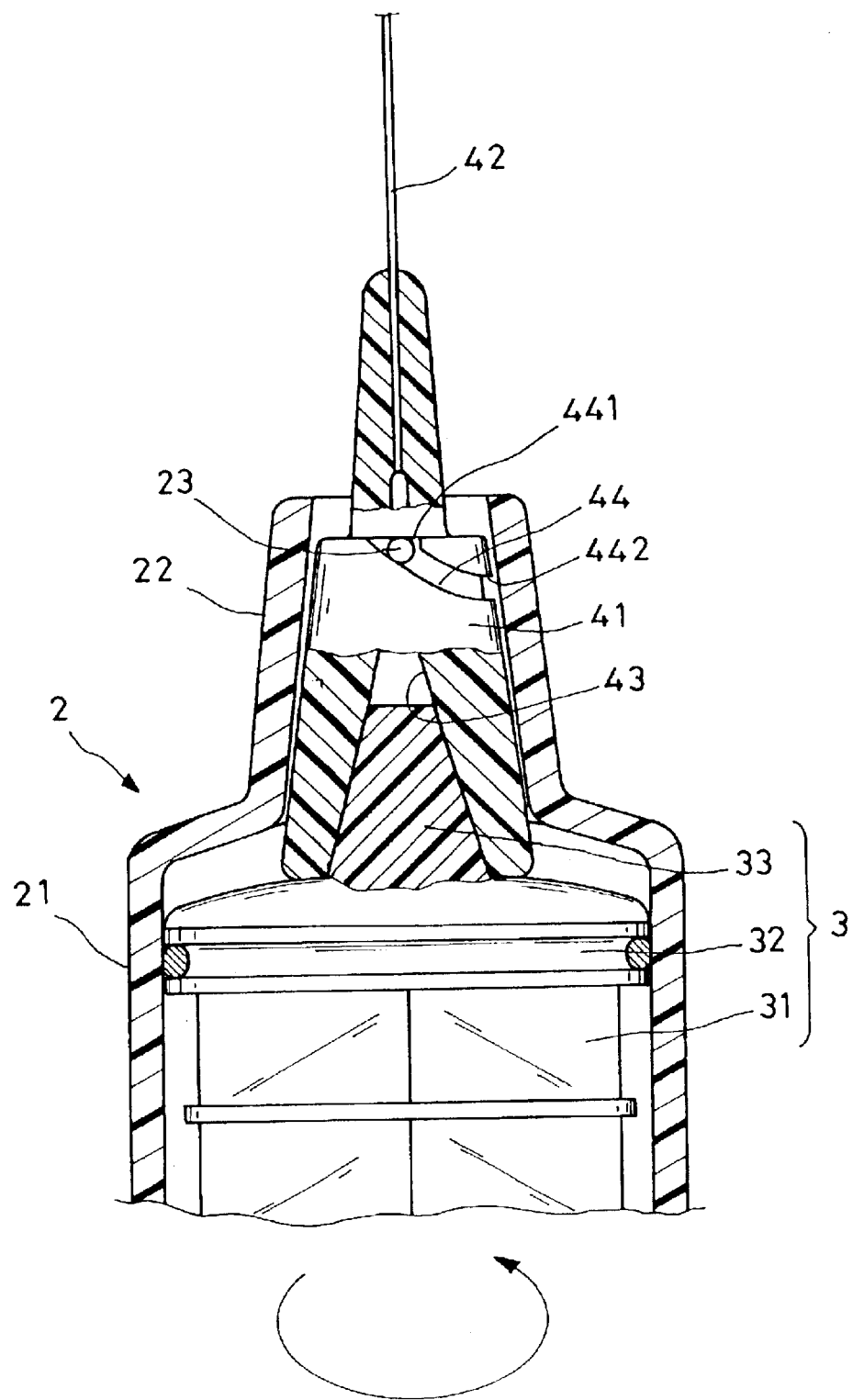
FIG. 12B is a schematic side view of the present invention, showing the plunger rotated counter-clockwise relative to the barrel after injection.
Figure 13:
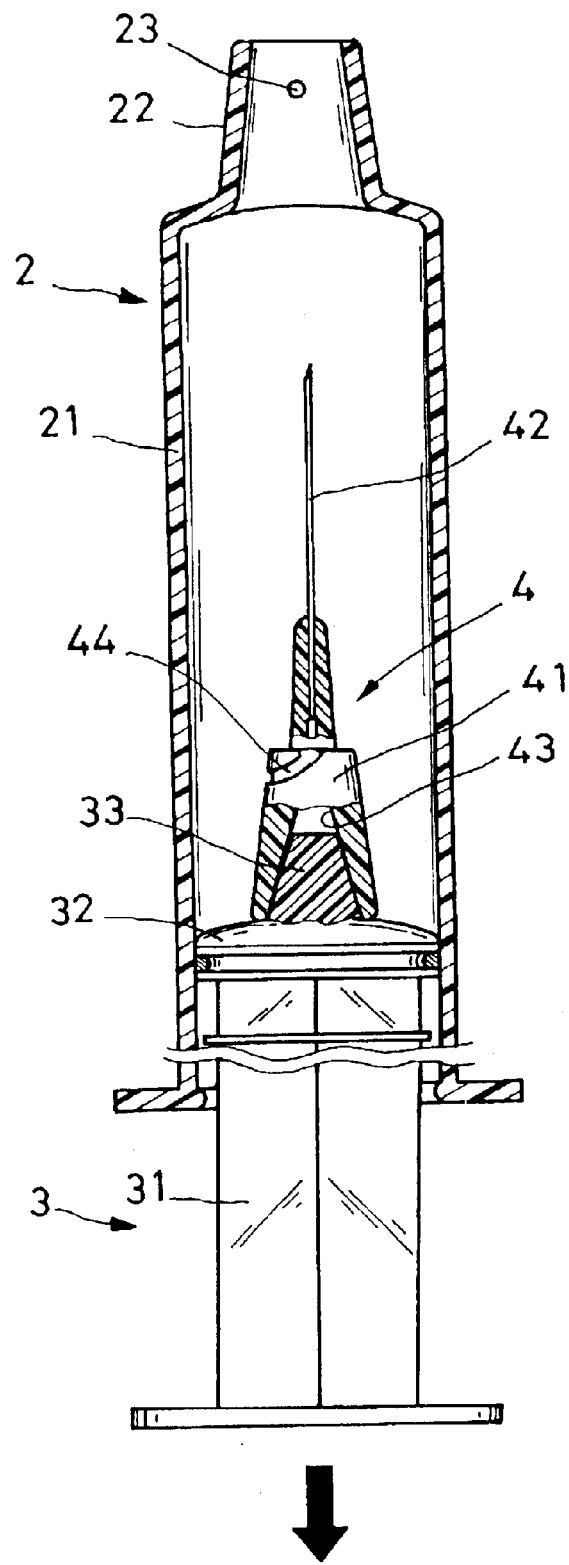
FIG. 13 is a schematic drawing of the present invention, showing the needle assembly received inside the barrel upon a back stroke of the plunger and stopper unit.

Referring to FIG. 9, when pulling the plunger 31 forwards in the barrel 2, the stopper 32 forces the liquid medicine out of the needle cannula 42.

Referring to FIGS. 10~13, when the plunger 31 moved to the front limit position and the liquid medicine completely (or approximately completely) forced out of the safety hypodermic syringe, the front engagement tip 33 of the plunger and stopper unit 3 is press-fitted into the bottom coupling hole 43 of the needle hub 41, keeping the planes 431 of the needle hub 41 abutted against the planes 331 of the front engagement tip 33. When rotating the plunger 31 clockwise (see FIG. 12A) or counter-clockwise (see FIG. 12B), the needle hub 41 is rotated with the front engagement tip 33 relative to the socket 22, thereby causing the needle assembly 4 to be moved axially backwards toward the inside of the body 21 of the barrel 2 and disengaged from the stub rods 23 of the socket 22, and therefore the needle assembly 4 is completely received inside the body 21 of the barrel 2 when the plunger 31 pulled backwards to the rear side of the barrel 2 (see FIG. 13).

A prototype of safety hypodermic syringe has been constructed within the features of FIGS. 3~13. The safety hypodermic syringe functions smoothly to provide all the features discussed earlier.

Although particular embodiments of the invention have been described in detail for purposes of illustration, various modifications and enhancements may be made without departing from the spirit and scope of the invention. Accordingly, the invention is not to be limited except as by the appended claims.

What is claimed is:

1. A safety hypodermic syringe comprising:
   a barrel, said barrel comprising a body and a socket at a front side of said body;
   a needle assembly, said needle assembly comprising a needle hub mounted in said front socket of said barrel, said needle hub having a bottom coupling hole, and a needle cannula forwardly extended from said needle hub outside said barrel; and
   a plunger and stopper unit, said plunger and stopper unit comprising a stopper fitted into said body of said barrel, and an elongated plunger backwardly extended from said stopper to the outside of said barrel and adapted to reciprocate said stopper in said body of said barrel, said stopper having a front engagement tip adapted to engage the bottom coupling hole of said needle hub for enabling said needle assembly to be pulled backwards with said plunger and stopper unit and received inside said body of said barrel;

wherein said socket of said barrel has at least one small stub rod protruding from an inside wall thereof; said needle hub of said needle assembly comprises at least one sliding groove formed in the periphery thereof and respectively coupled to the at least one small stub rod of said socket, for enabling said needle assembly to be pulled backwards with said plunger and stopper unit and received inside said body of said barrel after a rotary motion of said plunger relative to said barrel, said at least one sliding groove each having two distal open ends through which said at least one small stub rod of said socket is moved in and out of said at least one sliding groove when said plunger and stopper unit and said barrel are rotated relative to each other, and a positioning portion on the middle between said two distal open ends for engagement with the at least one small stub rod of said socket, said positioning portion and said two distal open ends being disposed at different elevations.

2. The safety hypodermic syringe as claimed in claim 1, wherein the bottom coupling hole of said needle hub is a conical hole, and the front engagement tip of said stopper is a conical tip fitting said conical hole.

3. The safety hypodermic syringe as claimed in claim 1, wherein said needle hub has at least one inside plane disposed inside said bottom coupling hole, and the front engagement tip of said stopper has at least one plane on the periphery thereof corresponding to the at least one inside plane of said needle hub.

4. The safety hypodermic syringe as claimed in claim 1, wherein the number of said at least one small stub rod of said socket is 2, and the two small stub rods are symmetrically disposed inside said socket at two sides.

5. The safety hypodermic syringe as claimed in claim 4, wherein the number of said at least one sliding groove of said needle hub is 2, and the two sliding grooves of said needle hub are symmetrically formed in the periphery of said needle hub at two sides corresponding to the two small stub rods of said socket.

6. The safety hypodermic syringe as claimed in claim 5, wherein said sliding grooves have a substantially U-shaped profile.

7. The safety hypodermis syringe as claimed in claim 5, wherein said sliding grooves have a substantially V-shaped profile.

* * * * *